(12) United States Patent
Shwartz et al.

(10) Patent No.: US 11,990,018 B2
(45) Date of Patent: May 21, 2024

(54) ADJUSTABLE ELECTRONIC MONITORING DEVICE

(71) Applicant: ATTENTI ELECTRONIC MONITORING LTD, Tel Aviv (IL)

(72) Inventors: Tsach Shwartz, Ramat Efal (IL); Ofer Friedman, Ganel-Tikva (IL); Yair Laster, Modiin (IL)

(73) Assignee: ATTENTI ELECTRONIC MONITORING LTD, Tel Aviv (IL)

( * ) Notice: Subject to any disclaimer, the term of this patent is extended or adjusted under 35 U.S.C. 154(b) by 0 days.

(21) Appl. No.: 17/615,593

(22) PCT Filed: Jul. 6, 2020

(86) PCT No.: PCT/IL2020/050756
§ 371 (c)(1),
(2) Date: Dec. 1, 2021

(87) PCT Pub. No.: WO2021/005596
PCT Pub. Date: Jan. 14, 2021

(65) Prior Publication Data
US 2022/0309896 A1    Sep. 29, 2022

Related U.S. Application Data

(60) Provisional application No. 62/871,245, filed on Jul. 8, 2019.

(51) Int. Cl.
*G08B 21/02* (2006.01)
*G08B 25/01* (2006.01)

(52) U.S. Cl.
CPC ..... *G08B 21/0286* (2013.01); *G08B 21/0291* (2013.01); *G08B 25/016* (2013.01)

(58) Field of Classification Search
CPC ............ G08B 21/0286; G08B 21/0291; G08B 25/016; G08B 21/22; G08B 29/046
See application file for complete search history.

(56) References Cited

U.S. PATENT DOCUMENTS 2,471,694 A * 5/1949 Maestri ................ A44C 5/2076
D11/5
4,577,256 A * 3/1986 Breidegam .............. A61N 1/14
361/220

(Continued)

FOREIGN PATENT DOCUMENTS

EA       028577 B1 * 12/2017 ............... G07C 9/28
EP       3382664 A1    10/2018

*Primary Examiner* — Mohamed Barakat
*Assistant Examiner* — Rufus C Point
(74) *Attorney, Agent, or Firm* — Soroker Agmon Nordman Riba; Daniel Schatz; Sharone R. Godesh

(57) ABSTRACT

A monitoring device, including an encasement having an upper part and a lower part; wherein the lower part is attached by a hinge at a first side of the encasement to the upper part; wherein at an opposite side the upper part can be lowered onto the lower part to close the encasement or lifted up to open the encasement; an elongated strap with a first end and a second end wherein the first end of the strap is attached to the first side of the encasement and configured to enable coupling the monitoring device to a person by wrapping the strap around a limb of a person, and inserting the second end of the strap into the opposite side of the encasement onto the lower part and covering it with the upper part.

20 Claims, 5 Drawing Sheets

(56) References Cited

U.S. PATENT DOCUMENTS

| | | | | |
|---|---|---|---|---|
| 5,627,520 A * | 5/1997 | Grubbs | ............... | G07C 9/28 455/100 |
| 5,650,766 A | 7/1997 | Burgmann | | |
| 5,686,897 A * | 11/1997 | Loh | ............... | G01R 31/52 340/649 |
| 6,826,120 B1 * | 11/2004 | Decker | ............... | H04M 1/677 379/433.1 |
| 7,636,047 B1 * | 12/2009 | Sempek | ............... | G08B 21/22 340/572.1 |
| 8,115,621 B2 * | 2/2012 | Rajala | ............... | H05K 5/066 340/539.11 |
| 10,360,788 B2 * | 7/2019 | Melfi | ............... | G08B 29/046 |
| 10,820,143 B2 * | 10/2020 | Segal | ............... | H04W 4/20 |
| 2003/0174059 A1 * | 9/2003 | Reeves | ............... | G08B 21/22 340/568.2 |
| 2003/0210142 A1 | 11/2003 | Freathy | | |
| 2007/0125816 A1 * | 6/2007 | Myers | ............... | A44C 5/0007 224/267 |
| 2007/0289342 A1 * | 12/2007 | Brooks | ............... | E05B 47/0002 70/16 |
| 2008/0009693 A1 * | 1/2008 | Hawthorne | ............... | A61B 5/14546 600/364 |
| 2009/0109633 A1 * | 4/2009 | Rajala | ............... | H05K 5/066 361/679.01 |
| 2010/0222073 A1 | 9/2010 | Aninye et al. | | |
| 2011/0109461 A1 * | 5/2011 | Aninye | ............... | G08B 21/0288 340/573.4 |
| 2011/0248853 A1 | 10/2011 | Roper et al. | | |
| 2014/0361892 A1 * | 12/2014 | Borlenghi | ............... | A45F 5/00 340/539.13 |
| 2015/0379857 A1 * | 12/2015 | Larose | ............... | G08B 21/185 340/652 |
| 2016/0078752 A1 * | 3/2016 | Vardi | ............... | H04B 1/385 340/506 |
| 2016/0148480 A1 | 5/2016 | Li | | |
| 2017/0039833 A1 * | 2/2017 | Baczuk | ............... | E05B 73/00 |
| 2019/0365062 A1 * | 12/2019 | Kelly | ............... | A44C 5/2042 |
| 2021/0201650 A1 * | 7/2021 | Friedman | ............... | G08B 21/22 |

* cited by examiner

ADJUSTABLE ELECTRONIC MONITORING DEVICE

RELATED APPLICATIONS

This application claims priority from Provisional application No. 62/871,245 filed on Jul. 8, 2019 the disclosure of which is incorporated herein by reference.

TECHNICAL FIELD

The present disclosure relates generally to an electronic monitoring device for attaching to a limb of a person and more specifically wherein the electronic monitoring device can be adjusted to fit different size limbs.

BACKGROUND

It is common practice today to attach a body worn electronic monitoring device to a person for monitoring their location and/or enforcing a location based policy such as house arrest, curfew sentencing, pre-trial sentencing, parole and probation. Typically the electronic monitoring device is attached with a strap to the ankle of the person or to other limbs, for example the wrist of the person. The person is prohibited from removing the electronic monitoring device to prevent them from violating a location based policy.

Standard electronic monitoring devices usually use a flexible strap with an inner optic fiber to protect against tampering. Electronic monitoring devices are configured to attach for example around the person's ankle. The strap is cut to length just before installation, attached at the ends to pin trays which are then coupled to the electronic monitoring device body. This process requires tools, dealing with many small parts and also intensive training, since the quality of the assembly of the strap after cutting impacts the optical connection to the device body. If the strap is not assembled correctly, false strap tamper indications, due to a poor optical connection will occur over time. This may cause significant operational overhead.

An alternative method is to have a set of pre-cut straps that are professionally assembled. Thus there is no need to assemble the straps in the field (in real time), just to pick the one with the right required length. However, this also leads to operational overhead since the officers now need to manage a large quantity of straps, with different lengths and keep track of the availability of all lengths. When straps are expensive (for example specially designed un-cuttable straps), this also becomes a financial challenge.

Another challenge is the installation time. The time required to take measurements and assemble the monitoring device. This has financial as well as safety implications.

Furthermore, disassembly is usually done by cutting the strap, making it disposable and increasing costs. Alternatively, a strap can be removed using a special tool, adding to the operational complexity.

SUMMARY

An aspect of an embodiment of the disclosure relates to an adjustable monitoring device for quick installation on a limb of a person. The monitoring device includes a strap and an enclosure with an upper part and a lower part that can be locked together to prevent access to an end of the strap. When the enclosure is open the end of the strap can be locked within the enclosure at selective positions extending or shortening the strap so that it will match the diameter of the person's limb. When the enclosure is open the strap can be released so that it can be removed from the person's limb.

There is thus provided according to an exemplary embodiment of the disclosure, a monitoring device, comprising:
  an encasement having an upper part and a lower part; wherein the lower part is attached by a hinge at a first side of the encasement to the upper part; wherein at an opposite side the upper part can be lowered onto the lower part to close the encasement or lifted up to open the encasement;
  an elongated strap with a first end and a second end wherein the first end of the strap is attached to the first side of the encasement and configured to enable coupling the monitoring device to a person by wrapping the strap around a limb of a person, and inserting the second end of the strap into the opposite side of the encasement onto the lower part and covering it with the upper part.

In an exemplary embodiment of the disclosure, the strap includes a number of notches on the second end of the strap and the lower part of the encasement includes a lock pin, which can be inserted into any one of the notches to match a thickness of the limb. Optionally, the strap includes a fiber optic cable embedded within and a base for attaching it to the first side of the encasement and wherein the base monitors the fiber optic cable to prevent tamper. In an exemplary embodiment of the disclosure, the upper part is configured to automatically lock together with the lower part when closing the encasement. Optionally, the monitoring device includes a locking mechanism that locks and unlocks the upper part onto the lower part responsive to activation or deactivation by a key or special tool.

In an exemplary embodiment of the disclosure, the monitoring device includes a locking mechanism that locks and unlocks the upper part onto the lower part responsive to receiving wireless commands. Optionally, the monitoring device locks or unlocks the locking mechanism responsive to receiving the wireless commands from two sources simultaneously or sequentially. In an exemplary embodiment of the disclosure, the locking mechanism locks or unlocks the upper part onto the lower part responsive to receiving wireless commands from an application on a mobile device in the vicinity of the monitoring device. Optionally, the locking mechanism locks and unlocks the upper part onto the lower part responsive to receiving wireless commands from a remote server at a monitoring center. In an exemplary embodiment of the disclosure, the lower part includes a frame surrounding an opening and the upper part includes a locking mechanism with a bolt that is configured to extend through the opening to lock the upper part together to the lower part.

There is further provided according to and exemplary embodiment of the disclosure, a method of connecting a monitoring device to a limb of a person, comprising:
  receiving an encasement having an upper part and a lower part; wherein the lower part is attached by a hinge at a first side of the encasement to the upper part; wherein at an opposite side the upper part can be lowered onto the lower part to close the encasement or lifted up to open the encasement;
  receiving an elongated strap with a first end and a second end;
  attaching the first end of the strap to the first side of the encasement;
  wrapping the strap around a limb of a person;

inserting the second end of the strap into the opposite side of the encasement onto the lower part and covering it with the upper part.

BRIEF DESCRIPTION OF THE DRAWINGS

The present disclosure will be understood and better appreciated from the following detailed description taken in conjunction with the drawings. Identical structures, elements or parts, which appear in more than one figure, are generally labeled with the same or similar number in all the figures in which they appear, wherein.

DETAILED DESCRIPTION

Figure 1A:
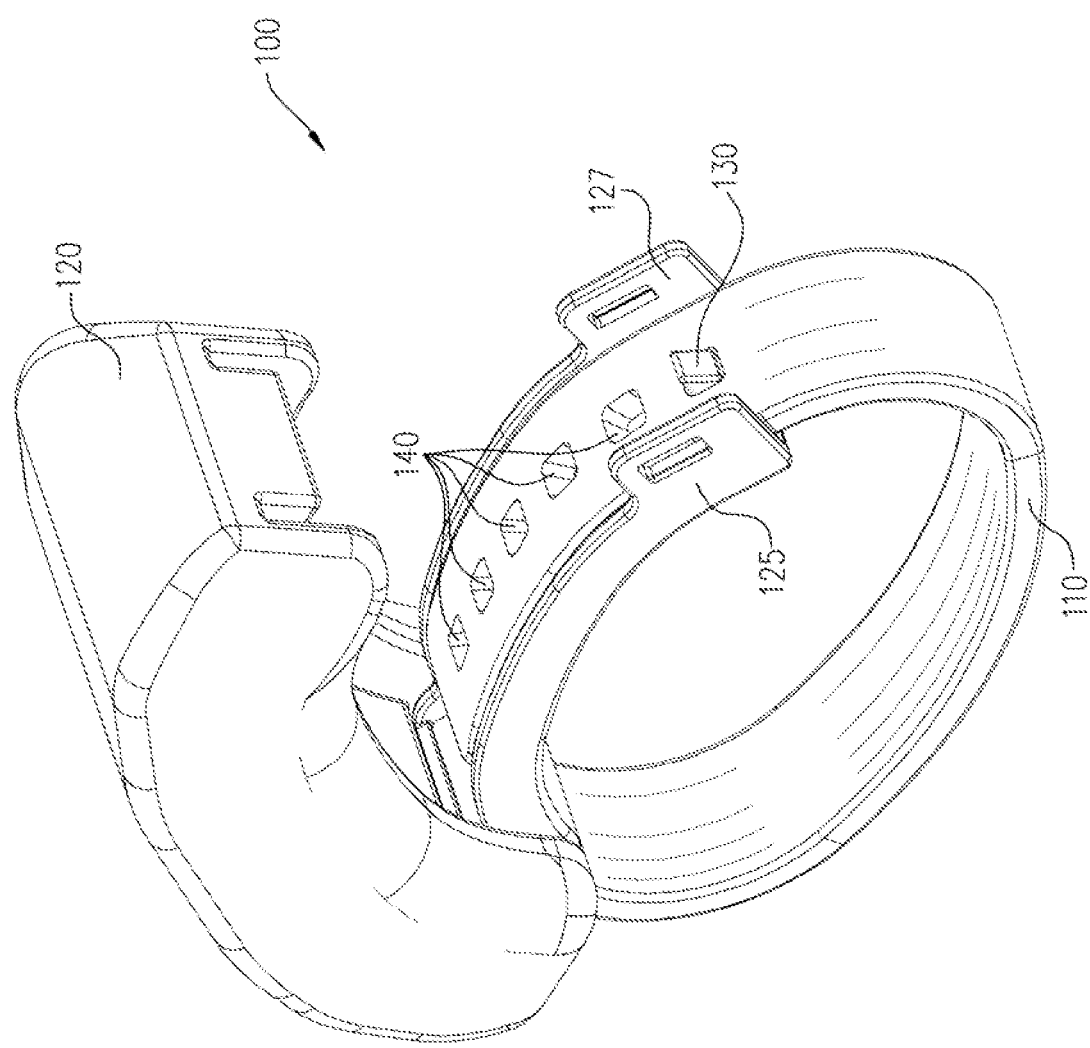
FIG. 1A is a schematic illustration of an unlocked monitoring device, according to an exemplary embodiment of the disclosure.
Figure 1B:
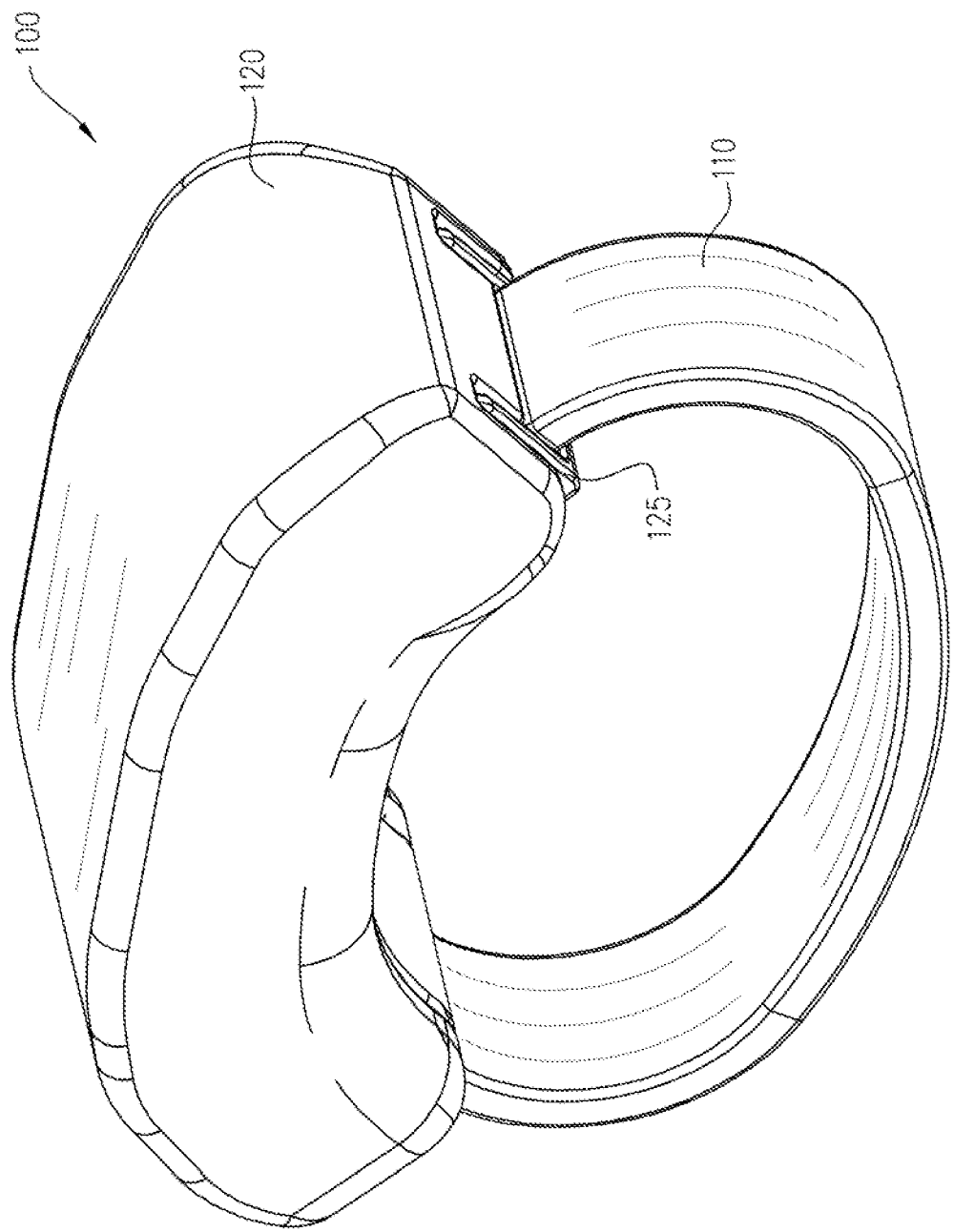
FIG. 1B is a schematic illustration of a locked monitoring device, according to an exemplary embodiment of the disclosure.

FIG. 1A is a schematic illustration of an unlocked monitoring device 100 and FIG. 1B is a schematic illustration of a locked monitoring device 100, according to an exemplary embodiment of the disclosure. In an exemplary embodiment of the disclosure, monitoring device 100 includes a flexible strap 110 for wrapping around a person's limb (e.g. an ankle or arm). The strap further includes one or more notches 140 to adjust the length of the strap to the circumference of the person's limb. In an exemplary embodiment of the disclosure, the monitoring device 100 includes a lower part 125 and an upper part 120, which form a protective enclosure over an end of the strap 110. In an exemplary embodiment of the disclosure, the strap 110 is secured to a first side of the lower part 125, configured to be wrapped around the person's limb, and be locked onto a lock pin 130 at an opposite side of the lower part 125 by inserting the lock pin 130 into one of the notches 140 according to the size of the person's limb. In some embodiments of the disclosure, both sides of the strap are locked with lock pins 130. Optionally, the first side may have only a single notch whereas on the opposite side there are multiple notches 140 so the length of the circumference is selectable. Alternatively, the first side may be coupled with a hinge 117 or a base 115 (e.g. as shown in FIG. 2B).

In an exemplary embodiment of the disclosure, upper part 120 is configured to fit over and lock onto the lower part 125. The upper part 120 is rotatably attached to the lower part 125 so that the upper part 120 can be lifted and lowered over the lower part 125, concealing the end of the strap 110 and notches 140 to prevent tampering. In an exemplary embodiment of the disclosure, strap 110 of monitoring device 100 is configured to provide the freedom to extend or shorten the circumference of the monitoring device by about 5-15 cm, accordingly, the monitoring device 100 then can be used for over 90% of the population. Optionally, the device can easily be unlocked, removed from a first person and relocked on the limb of another person.

Figure 2A:
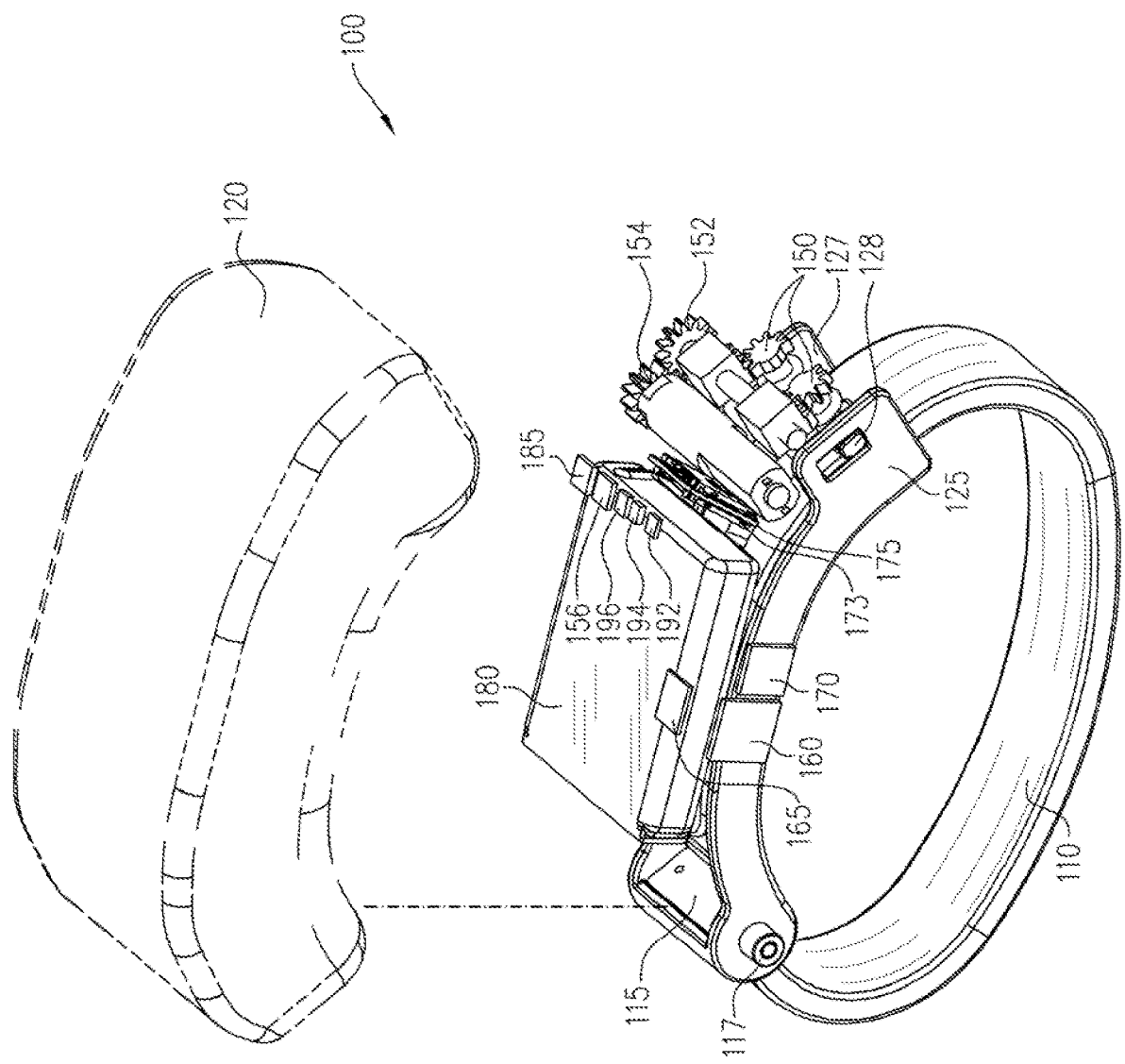
FIG. 2A is a schematic illustration of a perspective transparent view of a monitoring device, according to an exemplary embodiment of the disclosure.
Figure 2B:
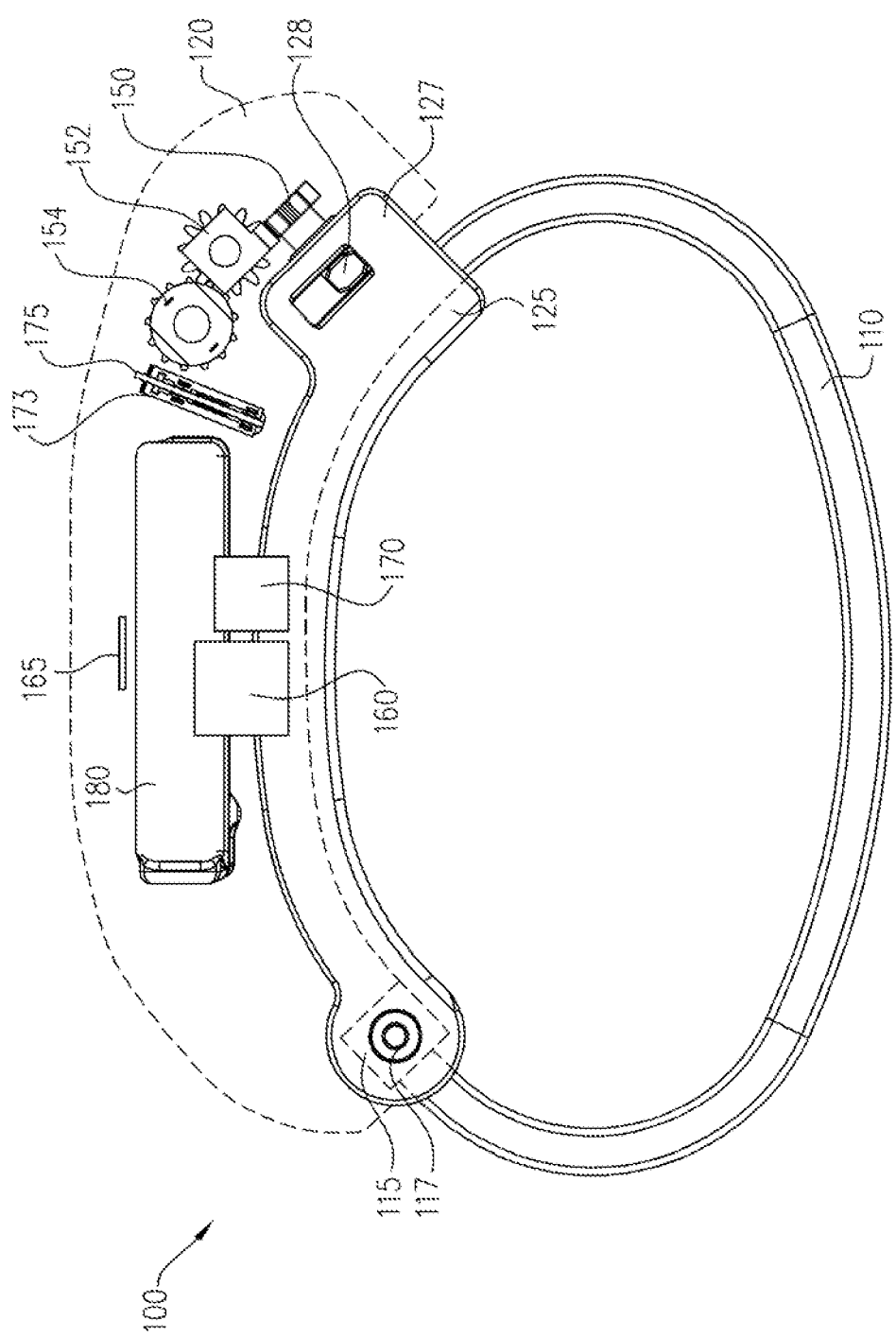
FIG. 2B is a schematic illustration of a side transparent view of a monitoring device, according to an exemplary embodiment of the disclosure.

FIG. 2A is a schematic illustration of a perspective transparent view of a monitoring device 100 and FIG. 2B is a schematic illustration of a side transparent view of a monitoring device 100, according to an exemplary embodiment of the disclosure.

In an exemplary embodiment of the disclosure, the monitoring device 100 includes a locking mechanism 150 to lock the upper part 120 onto lower part 125. Optionally, the locking mechanism 150 is an electronic locking mechanism that is controlled by an electronic circuit, for example motor driver circuit 156 and/or controller 170. Optionally, the locking mechanism 150 can be activated or deactivated wirelessly, for example by a mobile device application or by a remote server directly communicating with the monitoring device 100. Thus the monitoring device 100 can be deployed or released without the need to use a dedicated key or tool.

In some embodiments of the disclosure, the upper part 120 is configured to snap shut over the lower part 125 and automatically lock the upper part 120 onto the lower part 125. Accordingly, the device may be easily deployed by pushing the upper part 120 onto the lower part 125 without the use of a tool. Optionally, lower part 125 includes a frame 127 surrounding an opening through which a bolt 128 of locking mechanism 150 can be inserted to lock the upper part 120 onto the lower part 125. In some embodiments of the disclosure, a motor 154 is used to activate and deactivate the locking mechanism 150. Optionally, additional gears 152 may relay the motion of the motor 154 to the locking mechanism 150. In some embodiments of the disclosure, a spring (not shown) may automatically lock the upper part 120 onto the lower part 125 when positioned so that the bolt 128 can be inserted into the opening of the frame 127.

In an exemplary embodiment of the disclosure, upper part 120 includes a socket 173 for inserting a subscriber identification module (SIM) card 175, so that the monitoring device 100 may communicate directly over a cellular network with an application of an administrator that is near the device or by commands from a remote administrator at a monitoring center. Optionally, the monitoring device 100 may also include a communication module 165 and one or more antennas 160 for communicating using Wi-Fi, Bluetooth, cellular or other wireless protocols. In some embodiments of the disclosure, unlocking the locking mechanism 150 requires use of two separate encrypted commands to prevent hacking, for example unlocking may require sending a command from a local application and from a remote server sequentially or simultaneously. Optionally, the monitoring device may require receiving a wireless signal over two different types of wireless protocols (e.g. Bluetooth and Wi-Fi), for example to confirm that the administrator is located in the vicinity of the device when it is unlocked.

In an exemplary embodiment of the disclosure, monitoring device 100 includes a rechargeable power source 180 and a charging circuit 185. Optionally, the person using the monitoring device 100 is required to charge the monitoring device 100 periodically to prevent the monitoring device 100 from discharging and losing contact with a central sever. Optionally if the monitoring device 100 loses contact with the central server the person may be considered in violation as if he or she tampered with and removed the monitoring device 100. Monitoring device 100 is configured to notify the server at the monitoring center if the battery is low or the device was tampered with.

In an exemplary embodiment of the disclosure, monitoring device 100 includes additional sensors, such as an accelerometer 196, a pressure sensor 194, an ambient light sensor 192 or other sensors. The additional sensors may be used to identify attempts to break the upper part 120, identify removal of the upper part 120 or opening of the upper part 120. For example ambient light sensor 192 may provide an indication if the monitoring device is closed or open. Alternatively or additionally, a magnetic sensor, a capacitive sensor or an inductive sensor may identify if the bolt 128 of the locking mechanism 150 is deployed or not. Additionally, sensors may identify the position of the strap 110 and be able to wirelessly notify the administrator with measurements of the circumference of the person's limb. The measurements may be used as an identification parameter to verify that the correct person is being monitored especially in a case that the monitoring device 100 was removed and redeployed. The monitoring device 100 may notify if when redeploying the length of the strap is not the same or changed significantly.

In an exemplary embodiment of the disclosure, to deploy the monitoring device 100 on a person, the administrator only needs to bring a single monitoring device 100. The administrator may open the monitoring device 100 with an application on a mobile device (e.g. a smartphone) that communicates with the monitoring device 100, or by calling a server to remotely issue a command for the monitoring device to be unlocked. Alternatively, the administrator may have a special tool or dedicated key In an exemplary embodiment of the disclosure, strap 110 includes a base 115 that is coupled to the first side of the lower part 125. The base 115 anchors strap 110 into lower part 125. Optionally, base 115 may be coupled to hinges 117 that allow the upper part 120 to rotate relative to lower part 125. In an exemplary embodiment of the disclosure, the hinges are covered by upper part 120 of the enclosure so that they cannot be dismantled by a person wearing the monitoring device 100.

In an exemplary embodiment of the disclosure, when monitoring device 100 is open, an administrator has access to replace the rechargeable power source 180 (e.g. battery) or SIM card 175, in addition to being able to adjust the length of the strap 110 to fit the limb of the person wearing the monitoring device 100. Additionally, the administrator may be able to dismantle the hinges 117 to completely separate the upper part 120 from the lower part 125.

Figure 3:
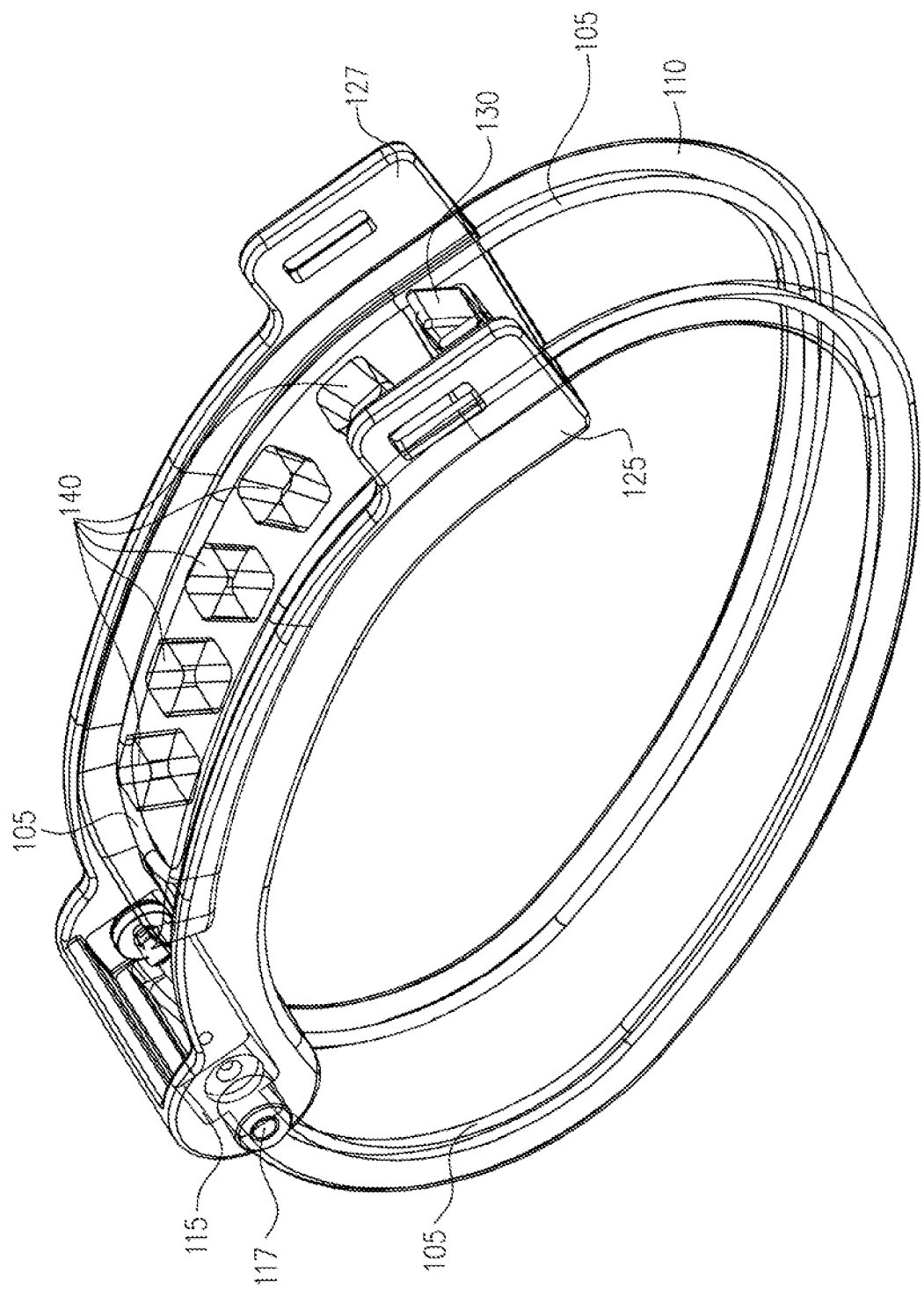
FIG. 3 is a schematic illustration of a perspective transparent view of a lower part of a monitoring device with a strap, according to an exemplary embodiment of the disclosure.

FIG. 3 is a schematic illustration of a perspective transparent view of lower part 125 of monitoring device 100 with strap 110, according to an exemplary embodiment of the disclosure. In an exemplary embodiment of the disclosure, strap 110 includes a fiber optic cable 105 that forms a loop within strap 110 to identify tampering with the strap 110 (e.g. cutting the strap 110 and fiber optic cable 105). Optionally, base 115 includes a circuit to send a light beam through the fiber optic cable 105 and verify that the loop has not been damaged. If the base 115 identifies a damaged loop it notifies controller 170 to report to the administrator or server at the monitoring center.

In an exemplary embodiment of the disclosure, the strap 110 may be made from silicon, rubber, metal, plastic or other materials. Optionally, the strap may be uncuttable by most tools especially standard household tools. Alternatively, the strap may be cuttable, however the monitoring device 100 is configured to notify a central server if the strap 110 is tampered with.

It should be appreciated that the above described methods and apparatus may be varied in many ways, including omitting or adding steps, changing the order of steps and the type of devices used. It should be appreciated that different features may be combined in different ways. In particular, not all the features shown above in a particular embodiment are necessary in every embodiment of the disclosure. Further combinations of the above features are also considered to be within the scope of some embodiments of the disclosure. It will also be appreciated by persons skilled in the art that the present disclosure is not limited to what has been particularly shown and described hereinabove but rather will be defined by the claims.

We claim:

1. A monitoring device, comprising:
an encasement having an upper part and a lower part; wherein the lower part is attached by a hinge at a first side of the encasement to the upper part; wherein at an opposite side the upper part can be lowered onto the lower part to close the encasement or lifted up to open the encasement; wherein the hinge is covered by the upper part;
an elongated strap with a first end and a second end wherein the first end of the strap is attached to the first side of the encasement and configured to enable coupling the monitoring device to a person by wrapping the strap around a limb of a person, and inserting the second end of the strap into the opposite side of the encasement onto the lower part and covering it with the upper part;
wherein the strap includes a number of notches on the second end of the strap and the lower part of the encasement includes a lock pin that extends upward from the lower part, and is configured to be inserted into any one of the notches to match a thickness of the limb; and prevent movement of the strap when closing the encasement;
wherein the lock pin is configured to penetrate the notches and protrude from an upper side of the strap.

2. The monitoring device according to claim 1, wherein the strap includes a fiber optic cable embedded within and a base for attaching it to the first side of the encasement and wherein the base monitors the fiber optic cable to prevent tamper.

3. The monitoring device according to claim 1, wherein the upper part is configured to automatically lock together with the lower part when closing the encasement.

4. The monitoring device according to claim 1, wherein the monitoring device includes a locking mechanism that locks and unlocks the upper part onto the lower part responsive to activation or deactivation by a key or special tool.

5. The monitoring device according to claim 1, wherein the monitoring device includes a locking mechanism that locks and unlocks the upper part onto the lower part responsive to receiving wireless commands.

6. The monitoring device according to claim 5, wherein the monitoring device locks or unlocks the locking mechanism responsive to receiving the wireless commands directly from two sources simultaneously or sequentially.

7. The monitoring device according to claim 5, wherein the locking mechanism locks or unlocks the upper part onto the lower part responsive to receiving wireless commands from an application on a mobile device in the vicinity of the monitoring device.

8. The monitoring device according to claim 5, wherein the locking mechanism locks and unlocks the upper part onto the lower part responsive to receiving wireless commands from a remote server at a monitoring center.

9. The monitoring device according to claim 1, wherein the lower part includes a frame surrounding an opening on the frame and the upper part includes a locking mechanism with a bolt that is configured to extend through the opening to lock the upper part together to the lower part.

10. The monitoring device according to claim 1, comprising an ambient light sensor that provides an indication if the encasement is closed or opened.

11. A method of connecting a monitoring device to a limb of a person, comprising:
   receiving an encasement having an upper part and a lower part; wherein the lower part is attached by a hinge at a first side of the encasement to the upper part; wherein at an opposite side the upper part can be lowered onto the lower part to close the encasement or lifted up to open the encasement; wherein the hinge is covered by the upper part;
   receiving an elongated strap with a first end and a second end;
   attaching the first end of the strap to the first side of the encasement;
   wrapping the strap around a limb of a person;
   inserting the second end of the strap into the opposite side of the encasement onto the lower part and covering it with the upper part;
   wherein the strap includes a number of notches on the second end of the strap and the lower part of the encasement includes a lock pin that extends upward from the lower part, and is configured to be inserted into any one of the notches to match a thickness of the limb; and prevent movement of the strap when closing the encasement;
   wherein the lock pin is configured to penetrate the notches and protrude from an upper side of the strap.

12. The method according to claim 11, wherein the strap includes a fiber optic cable embedded within and a base for attaching it to the first side of the encasement and wherein the base monitors the fiber optic cable to prevent tamper.

13. The method according to claim 11, wherein the upper part is configured to automatically lock together with the lower part when closing the encasement.

14. The method according to claim 11, wherein the monitoring device includes a locking mechanism that locks and unlocks the upper part onto the lower part responsive to activation or deactivation by a key or special tool.

15. The method according to claim 11, wherein the monitoring device includes a locking mechanism that locks and unlocks the upper part onto the lower part responsive to receiving wireless commands.

16. The method according to claim 15, wherein the monitoring device locks or unlocks the locking mechanism responsive to receiving the wireless commands directly from two sources simultaneously or sequentially.

17. The method according to claim 15, wherein the locking mechanism locks or unlocks the upper part onto the lower part responsive to receiving wireless commands from an application on a mobile device in the vicinity of the monitoring device.

18. The method according to claim 15, wherein the locking mechanism locks and unlocks the upper part onto the lower part responsive to receiving wireless commands from a remote server at a monitoring center.

19. The method according to claim 11, wherein the lower part includes a frame surrounding an opening on the frame and the upper part includes a locking mechanism with a bolt that is configured to extend through the opening to lock the upper part together to the lower part.

20. The method according to claim 11, wherein an ambient light sensor provides an indication if the encasement is closed or opened.

* * * * *